United States Patent
Meadows et al.

(10) Patent No.: US 6,920,359 B2
(45) Date of Patent: Jul. 19, 2005

(54) DEEP BRAIN STIMULATION SYSTEM FOR THE TREATMENT OF PARKINSON'S DISEASE OR OTHER DISORDERS

(75) Inventors: Paul M. Meadows, Glendale, CA (US); Carla M. Mann, Los Angeles, CA (US)

(73) Assignee: Advanced Bionics Corporation, Valencia, CA (US)

( * ) Notice: Subject to any disclaimer, the term of this patent is extended or adjusted under 35 U.S.C. 154(b) by 313 days.

(21) Appl. No.: 09/936,803
(22) PCT Filed: Jan. 12, 2001
(86) PCT No.: PCT/US01/04417
§ 371 (c)(1),
(2), (4) Date: Sep. 14, 2001
(87) PCT Pub. No.: WO01/60450
PCT Pub. Date: Aug. 23, 2001

(65) Prior Publication Data
US 2002/0161403 A1 Oct. 31, 2002

Related U.S. Application Data
(60) Provisional application No. 60/182,486, filed on Feb. 15, 2000.

(51) Int. Cl.[7] ............................................... A61N 1/36
(52) U.S. Cl. .................................... 607/59; 607/60
(58) Field of Search ........................... 607/30–32, 59, 607/60, 1, 2, 45, 46, 48, 116, 139, 148

(56) References Cited

U.S. PATENT DOCUMENTS 5,358,514 A    10/1994   Schulman et al. ............ 607/61
5,807,397 A     9/1998   Barreras ...................... 607/61
6,016,449 A  *  1/2000   Fischell et al. .............. 607/45
6,128,537 A  * 10/2000   Rise ............................. 607/45
6,560,486 B1 *  5/2003   Osorio et al. ................ 607/45

FOREIGN PATENT DOCUMENTS

EP     0911061        4/1999
EP     0000911061  *  4/1999
WO     9521591        8/1995
WO     9843700       10/1998

* cited by examiner

Primary Examiner—George R. Evanisko
(74) Attorney, Agent, or Firm—Bryant R. Gold

(57) ABSTRACT

A deep brain stimulation (DBS) system (10) provides a multiplicity of stimulation channels through which stimulation may be delivered deep within the brain of the patient. The DBS system is powered by a rechargeable battery (27). In one embodiment, the system has four channels driving sixteen electrodes (32). The DBS system is easily programmed for use by a clinician using a clinician programming system (60), and further affords a simple but highly advanced hand held programmer (50) control interface through which the patient may easily change stimulation parameters within acceptable limits. The DBS system (10) includes a small, implantable pulse generator (20) that is small enough to be implanted directly in the cranium of the patient, thereby eliminating the long lead wires and tunneling procedures that have been used in the past. Further, the DBS system allows up to two electrode arrays (30, 30') to be attached to the implantable pulse generator (20), thereby eliminating the requirement for implanting two independent implantable pulse generators for bilateral stimulation of deep brain structures.

14 Claims, 3 Drawing Sheets

DEEP BRAIN STIMULATION SYSTEM FOR THE TREATMENT OF PARKINSON'S DISEASE OR OTHER DISORDERS

This application claims the benefit of Provisional application Ser. No. 60/182,486, filed Feb. 15, 2000.

BACKGROUND OF THE INVENTION

The present invention relates to deep brain stimulation (DBS) systems, and more particularly to a DBS system that utilizes a multichannel implantable pulse generator (IPG) small enough to be implanted directly in the cranium of the patient.

More than a decade ago, a single channel implantable pulse generator (IPG) was developed for the purpose of stimulating the spinal cord to treat chronic and intractable pain. Over the years, more and more applications for implantable systems that could deliver electrical stimulation to neural tissues were discovered, including the stimulation of structures deep within the brain controlling movement. For each of these applications, the single channel IPG with it's single channel stimulator was placed into a new package, sometimes with a new name, sometimes with a variation in its electrode, and provided as a new product, each time using the same electronics, power systems, telemetry methods, cumbersome programming methods, and often the same leadwires and surgical tools for those devices. So, while the technology offered through the single channel device was not as sophisticated as what it could deliver, it was still the best available technology, and as a result systems have existed that may not have been adequate for the job, but were better than no systems as all.

There is now a recognition that patients suffering from Parkinson's Disease, essential tremor, and other movement disorders, need better devices to treat their conditions. Such devices need to last many times longer, need to reduce the surgical time required for their implantation, and need to better address the problems for which they are applied in patients. Moreover, such devices should preferably be designed for the surgical location of the device and the structures to be stimulated, rather than just be a re-labeled system designed for another application altogether and simply marketed for a new application.

Thus, while single channel DBS systems are known in the art, such systems suffer from numerous defects and serious deficiencies.

For example, one system used today for DBS applications utilizes an implantable pulse generator powered by a primary battery (non-rechargeable), originally designed for spinal cord stimulation. The pulse generator is large and must be implanted in the shoulder region, thereby requiring long leads and an arduous surgical procedure of tunneling in order to interconnect the leads with the pulse generator and in order to place the leads and electrodes in the desired location in contact with brain tissue. For many patients with aggressive stimulation parameter settings, the lifetime of the primary battery is very short, thus requiring frequent replacement surgeries.

An alternative to the primary battery powered device is an RF-powered device which requires that the patient wear an antenna coil over the site of the implant and carry an external transmitter/controller.

When bilateral stimulation is required using existing DBS devices, which occurs often, two complete, independent pulse generators, including separate lead wires and electrode systems must presently be implanted.

Patient controllers for use with existing systems require that the patient controller be held directly over the implant site for the transfer of telemetry commands. This makes use of such patient controller for an implant site on the cranium extremely difficult, if not impossible. Additionally, use of such a patient controller with a shoulder-located stimulator is similarly deficient.

It is thus seen that numerous problems and deficiencies are present with existing DBS systems.

A brief review of the literature follows which describes the work of various clinicians and researchers in the application of DBS and early chronic cerebellar stimulation (CCS) for the treatment of pain and movement disorders. Basic research and issues with the technology of electrical stimulation are discussed.

CCS and DBS Early Work

Cooper, I, in various publications made in 1978, 1980, 1981, and 1984, (see, e.g., Cooper, I: Historical review of cerebellar stimulation. Cerebellar Stimulation for Spasticity and Seizures: 3–8, 1984 by Davis, R and Bloedel, J), reported that chronic cerebellar stimulation (CCS) and deep brain stimulation (DBS) were employed to reverse some of the symptoms of spasticity, hemiparesis, tremor, dystonia and torticollis by prosthetic mobilization of CNS inhibitory mechanisms in the cerebral cortex and thalamus. Again, in 1985, Cooper demonstrated that the long term chronic stimulation of the brain has resulted in no harmful effects in any case while at the same time demonstrating effectiveness (see Cooper et al., "The effect of chronic stimulation of cerebellum and thalamus upon neurophysiology and neurochemistry of cerebral cortex", Neurostimulation: An Overview: 207–212, 1985 by Lazorthes, Y and Upton, A.) Others had previously shown, in a double blind study, the efficacy of cerebellar stimulation for spasticity (see, e.g., McLellan, D et al., "Time course of clinical and physiological effects of stimulation of the cerebellar surface in patients with spasticity", Journal of Neurology 41, 150–160, 1978).

Bilateral DBS

It has recently been demonstrated that Bilateral DBS of the internal pallidum and the subthalamic nucleus improves a number of aspects of motor function, movement time, and force production, with few significant differences between internal pallidum and subthalamic nucleus groups; and that the effects are similar to unilateral pallidal lesions reported elsewhere (see, Brown, R. G. et at, "Impact of deep brain stimulation on upper limb akinesia in Parkinson's disease", Annals of Neuology, 45(4)473–487, April 1999.) One year earlier, in 1998, R Kumar reported on one of the few double blind studies that objectively verified the clinical effects of subthalamic nucleus (STN) DBS in advanced Parkinson's Disease (PD) (see Kumar, R, et. al., "Double-blind evaluation of subthalamic nucleus deep brain stimulation in advanced Parkinson's disease", Neurology, 51:850–855, 1988). Kumar's conclusions were that STN DBS is a promising option for the treatment of advanced PD and that the clinical benefits obtained outweighed the adverse effects. Later, Kumar also looked at bilateral globus pallidus internus (GPi) DBS for medication-refractory idiopathic generalized dystonia, and reported obtaining good results (see, Kumar et al., "Globus pallidus deep brain stimulation for generalized dystonia: clinical and PET investigation", Neurology, 53:871–874, 1999).

It has also been demonstrated that bilateral DBS in levodopa-responsive patients with severe motor fluctuations was safe and efficient (see, Ghika, J. et al., "Efficiency and safety of bilateral contemporaneous pallidal stimulation (deep brain stimulation) in levodopa-responsive patients with Parkinson's disease with severe motor fluctuations: a 2-year follow-up review", J. Neurosurg., Vol. 89, pp713–718, November 1998). In this report, Ghika indicated that improvements in motor score Activities of Daily Living (ADL) were obtained, and that off time persisted beyond two years after the operation, but that signs of decreased efficacy started to be seen after 12 months. Siegfried, J confirmed in 1994 that the use of bilateral DBS for PD was both nondestructive and reversible (Siegfried, J. et al., "Bilateral chronic electrostimulation of ventroposterolateral pallidum: a new therapeutic approach for alleviating all Parkinsonian symptons", Neurosurgery, 35(6):1126–1130, December 1994).

Unilateral DBS

Good results have also been demonstrated with unilateral thalamic DBS for refractory essential (ET) and Parkinson's Disease (PD) tremor, with 83% and 82% reductions respectively in contralateral arm tremor (see, Ondo W, et al., "Unilateral thalamic deep brain stimulation for refractory essential tremor and Parkinson's disease tremor", Neurology, 51:1063–1069, 1998). However, no meaningful improvement in other motor aspects was observed.

Unilateral and Bilateral Pallidotomy

In 1998, the results of unilateral ventral medial pallidotomy was reviewed in 22 patients at 3 months postoperatively and at 14 months (see, Schrag A, et al., "Unilateral pallidotomy for Parkinson's disease: results after more than 1 year", J. Neurol Neurosurg Psychiatry, 67:511–517, 1999). It was concluded that the beneficial effects persist for at least 12 months, and that dyskinesias are most responsive to this procedure. The reduction of contralateral dyskinesias was, however, slightly attenuated after 1 year. Another study, involving 21 patients, demonstrated that the pain associated with PD can be significantly reduced with unilateral pallidotomy (see, Honey et al., "Unilateral pallidotomoy for reduction of Parkinsonian pain", J Neurosurg. 91:198–201, 1999). Earlier, other researchers had demonstrated control of levodopa-induced dyskinesias by thalamic lesions delivered by microelectrode technique and controlled in size and accurately located with respect to ventralis oralis (Vo) complex and ventralis intermediate nucleus (Vim) (see, Narabayashi, et al., "Levodopa-induced dyskinesia and thalamotomy", J. Neurology, Neurosurgery, and Psychiatry 47:831–839, 1984).

R M Scott et al. (Scott et al., "The effect of thalamotomy on the progress of unilateral Parkinson's disease", J Neurosurg, 32:286–288, March 1970) reviewed 72 patients exhibiting long term post unilateral thalamotomy to determine whether the procedures were adequate. Their results indicated, as suggested previously by Cooper, that unilateral procedures were inadequate and that when symptoms were absent from the side not receiving the procedure, they often appeared later when they were no longer benign. E Levita (Levita et al., "Psychological comparison of unilateral and bilateral thalamic surgery", Journal of Abnormal Psychology 72 (3), 251–254, 1967) reported no significant differences between unilateral versus bilateral thalamic surgery in cognitive and perceptual functions and performance on visual and auditory tasks of recent recall.

DBS and Effects on Memory, Other Functions

One group of researchers suggested that in the application of chronic DBS of the left ventrointermediate (Vim) thalamic nucleus for the treatment of PD on semantic (verbal fluency and confrontation naming) and episodic (word list) memory tasks that DBS might interfere with access to episodic memory, but enhance access to semantic memory (see, Troster et al., "Chronic electrical stimulation of the left ventrointermediate (Vim) thalamic nucleus for the treatment of pharmacotherapy-resistant Parkinson's disease: a differential impact on access to semantic and episodic memory?". Brain and Cognition, 38:125–149, 1998). Troseter et al., suggested that future studies look at effects of number and locations of electrodes. Earlier, it had been reported that thalamic stimulation and thalamotomy had been utilized to study the H reflex (Laitinen et al., "Effects of thalamic stimulation and thalamotomy on the H reflex", Electroencephalography and Clinical Neurophysiology 28:586–591, 1970). Laitinen's report found that the H reflex was facilitated by repetitive stimulation of the contralateral VL, while coagulation of VL diminished the H reflex in half of the patients, suggesting that there are at least two different pathways from the VL area which facilitate the spinal motoneurone.

Another report indicated that in five PD patients with "freezing" gait and postural instability, chronic unilateral DBS of the STN resulted in effectively alleviating this gait with improvement in walking in all of the patients tested (see, Yokoyama et al., "Subthalamic nucleus stimulation for gait disturbance in Parkinson's disease", Neurosurgery, 45(1):41–49, July 1999). STN stimulation was also reported by other researchers to alleviate akinesia and rigidity in PD patients (Pollak et al., "Subthalamic nucleus stimulation alleviates akinesia and rigidity in Parkinsonian patients", Adv Neurology, 69:591–594, 1996).

Pain, Device Failures, Issues in Implementing the Technology

It has been reported that parafasicular-center median nuclei stimulation for intractable pain and dyskinesia and thalamic stimulation for chronic pain have been successful. (Andy O J, "Parafascicular-center median nuclei stimulation for intractable pain and dyskinesia (painful-dyskinesia)", Appl. Neurophysiol., 43:133–144, 1980; Dieckmann et al., "Initial and long-term results of deep brain stimulation for chronic intractable pain", Appl. Neurophysiol., 45:167–172, 1982). Additionally, the notion of two separate sensory modulating system was supported through the combined stimulation of the periaqueductal gray matter and sensory thalamus (Hosobuchi, Y "Combined electrical stimulation of the periaqueductal gray matter and sensory thalamus", Applied Neurophysiology 46:112–115, 1983).

G H Duncan (Duncan et al., "Deep brain stimulation: a review of basic research and clinical studies", Pain 45:49–59, 1991) reviewed 30 years of DBS for pain and concluded that there is considerable evidence, in both basic and clinical studies, suggesting that deep brain stimulation can modify the activity of nociceptive neurons, and that this approach should be a feasible alternative for the treatment of chronic, intractable pain. Duncan suggested that future research be constrained to primates, rather than in cats and rats to narrow the differences between basic and clinical studies and that overall, studies with mixed results appear to have poor controls without the benefit of rigorous experimental standards.

K. Kumar (Kumar et al., Deep brain stimulation for intractable pain: a 15-year experience", Neurosurgery, 40(4):7360747, 1997) followed 68 patients over 15 years and noted long term effective pain control with few side effects or complications. R. R. Tasker (Tasker et al., "Deep brain stimulation for neuropathic pain", Stereotack Funct. Neurosurg., 65:122–124, 1995) investigated the use a commercially-available electrode and stimulator, available from a well-known medical equipment manufacturer, for DBS for the treatment of pain. In his investigation, 62 patients were tested, and 25 patients implanted of paresthesia-producing (PP) and periventricular gray (PVG) were evaluated. In no case did PVG DBS produce pain relief: in 15 PP patients, some pain relief was produced. Of particular note were the problems associated with the use of the device: 2 cases of seizures due to migrated electrodes, 14 other electrode migrations, 2 receiver migrations, 1 receiver malfunction and 8 general equipment breakages, disconnections or extrusions.

R. M. Levy (Levy et al., "Treatment of chronic pain by deep brain stimulation: long term follow-up and review of the literature", Neurosurgery, 21:6, 885–893, 1987) reported on the long term follow-up of treatment of chronic pain with DBS of 141 patients having a mean length of follow-up of 80 months post implant. Technical problems most often encountered included migration of the implanted electrodes and equipment failure that led to leakage of current and ineffective stimulation. Lasting relief from pain was obtained in 47% of patients with deafferentiation and 60% with nociceptive pain. Caparros-Lefebvre (Caparros-Lefebvre et al., "Improvement of levodopa induced dyskinesias by thalamic deep brain stimulation is related to slight variation in electrode placement: possible involvement of the centre median and parafascicularis complex", J. Neurol. Neurosurg. Psychiatry, 67:308–314, 1999) investigated why two teams using the same procedure and the same target for DBS obtained different results on levodopa induced dyskinesias, whereas Parkinsonian tremor was improved or totally suppressed, and it was discovered that there was on average electrode placement difference of 2.9 mm in electrode depth, which did not seem to correspond to the coordinates of the VIM, but rather seemed to be closer to those of the centre median and parafascicularis (CM-Pf) complex. The Caparros-Lefebvre study seems to support the hypothesis that patients experiencing an improvement of dyskinesias under DBS are actually stimulated in a structure which is more posterior, more internal and deeper than the VIM, very close to the CM-Pf. However, J. Guridi (Guridi et al., "Stereotactic targeting of the globus pallidus internus in Parkinson's disease: imaging versus electrophysiological mapping", Neurosurgery, 45(2):278–289, August, 1999) determined that lesion targeting based on MRI alone is not sufficiently accurate to guarantee placement of the lesion in the sensorimotor region of the globus pallidus internus (Gpi).

J. Miles (Miles et al., "An electrode for prolonged stimulation of the brain", Applied Neurophysiology 45:449–455, 1982) described several of the problems with the electrode used in the Kumar study: 1) electrode roughness presents a danger of trauma along the cannula track; 2) definite risk of early displacement of the electrode tip from its target site, especially with the electrode is disengaged from the insertion tool, because the intrinsic springlike behavior of the electrode tends to cause it to retract along its insertion track; 3) displacement of the electrode tip from its insertion position can also occur over a period of time, presumably due to the dynamic pulsatile nature of the brain; 4) repositioning of an electrode which is not producing satisfactory stimulation effects is difficult because of the progressively increasing distortion and springlike behavior of the electrode; and 5) the electrodes are expensive. Miles went on to describe an electrode with a feature that would allow it to be anchored at the insertion target location thus preventing movement post insertion. J Siegfried (Siegfried et al., "Intracerebral electrode implantation system." Journal of Neurosurgery 59:356–359, 1983) also described an improved electrode along with a fixation device which could secure the electrode leadwire accurately with a fixture at the burr hole location.

DBS and Essential Tremor

R. Tasker ((Tasker "Deep brain stimulation is preferable to thalamotomy for tremor suppression", Surg. Neurol., 49:145–154, 1998) demonstrated that DBS is preferable to thalamotomy for tremor suppression in that tremor recurrence after DBS can be controlled by stimulation parameter adjustment rather than by re-operation, but thalamotomy recurrence can only be corrected by secondary surgery. Additionally, ataxia, dysarthria and gait disturbance were more common after thalamotomy (42%) than in DBS (26%) and that when they occurred after DBS they were nearly always controlled by adjusting stimulation parameters. J P Hubble (Hubble et al., "Deep brain stimulation for essential tremor", Neurology, 46:1150–1153, 1996) demonstrated that DBS applied in the left Vim thalamic nucleus could be applied for essential tremor (ET) safely and effectively.

Upper Limb

R. G. Brown (Brown, et al., "Impact of deep brain stimulation on upper limb akinesia in Parkinson's disease", Annals of Neurology, 45(4)473–487, April 1999) has also shown that upper limb akinesia in Parkinson's disease may be treated by DBS of the internal pallidum or subthalamic nucleus.

Basic Research

R. Iansek (Iansek et al., "The monkey globus pallidus: neuronal discharge properties in relation to movement", Journal of Physiology 301:439–455, 1980) demonstrated that the function of pallidal neurones is intimately concerned with movement performance, as very discrete movements were represented by the discharges of individual neurons. A Benazzouz (Benazzouz et al., "Responses of substantia nigra pars reticulata and globus pallidus complex to high frequency stimulation of the subthalamic nucleus in rats: electrophysiological data". Neuroscience Letters, 189:77–80, 1995) demonstrated that high frequency stimulation of the subthalamic nucleus (HFS-STN) induces a cl73 ear cut decrease in neuronal activity in its two main efferents, the substantia nigra pars reticulata (SNr) and entopeduncular nucleus (EP) in basic studies in rats, thus providing an explanation for the alleviation of Parkinsonian symptoms by chronic STN stimulation in human patients.

R R Tasker (Tasker et al., "Investigation of the surgical target for alleviation of involuntary movement disorders", Appl. Neurophysiol., 45:261–274, 1982) reviewed data from 198 stereotactic procedures with data from 9,383 sites, concluding that a common target in inferior VIM in the 13.5 mm sagittal plane for the control of a variety of dyskinesias existed.

From the above brief review of the literature, it is thus seen that although much research has been done to date, there exists a critical need in the art for a DBS system that can specifically address the needs of individual patients in order to provide relief or treatment for various disorders.

SUMMARY OF THE INVENTION

The present invention addresses the above and other needs by providing a deep brain stimulation (DBS) system that offers: (1) a longer operational life than has heretofore been available with implanted electronic systems, (2) leads and electrodes specifically suited for the DBS application, and (3) a multiplicity of stimulation channels through which stimulation may be delivered deep within the brain of the patient. The DBS system described herein advantageously is powered by a rechargeable lithium-ion battery. The system has 4 channels driving 16 electrodes. The system is capable of providing many years of operation. The system may be easily programmed for use by a clinician, and further affords a simple but highly advanced control interface through which the patient may easy change stimulation parameters within acceptable limits.

In accordance with one aspect of the invention, a small, implantable pulse generator (IPG) forms a key component of the DBS system. Advantageously, the IPG used with the DBS system is small enough to be implanted directly in the cranium of the patient, thereby eliminating the long lead wires and tunneling procedures that have been required with existing DBS systems.

In accordance with another key aspect of the invention, the DBS system allows up to two electrode arrays to be attached to the IPG, thereby eliminating the requirement for implanting two independent IPG's for bilateral stimulation of deep brain structures.

It is a feature of the invention to provide a DBS system that incorporates a replenishable power source, e.g., a rechargeable battery, as part of, or coupled to, an implanted pulse generator, whereby the power source may be replenished, as required, in order to afford a long operating life for the DBS system.

It is another feature of the invention, in accordance with one embodiment thereof, to provide a DBS system that is capable of delivering stimulation pulses to the brain through selected electrodes on up to two electrode arrays connected to a single, multichannel pulse generator, whereby bilateral stimulation of the brain may be provided, if desired.

BRIEF DESCRIPTION OF THE DRAWINGS

The above and other aspects, features and advantages of the present invention will be more apparent from the following more particular description thereof, presented in conjunction with the following drawings wherein.

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

The DBS system of the present invention includes a cranium mountable pulse generator, support for two electrode cables supporting bilateral brain stimulation, electrodes specifically designed for the small structures required for the DBS application, and an electrode fixation system guaranteeing reliable electrode and lead wire position once implanted.

Figure 1:
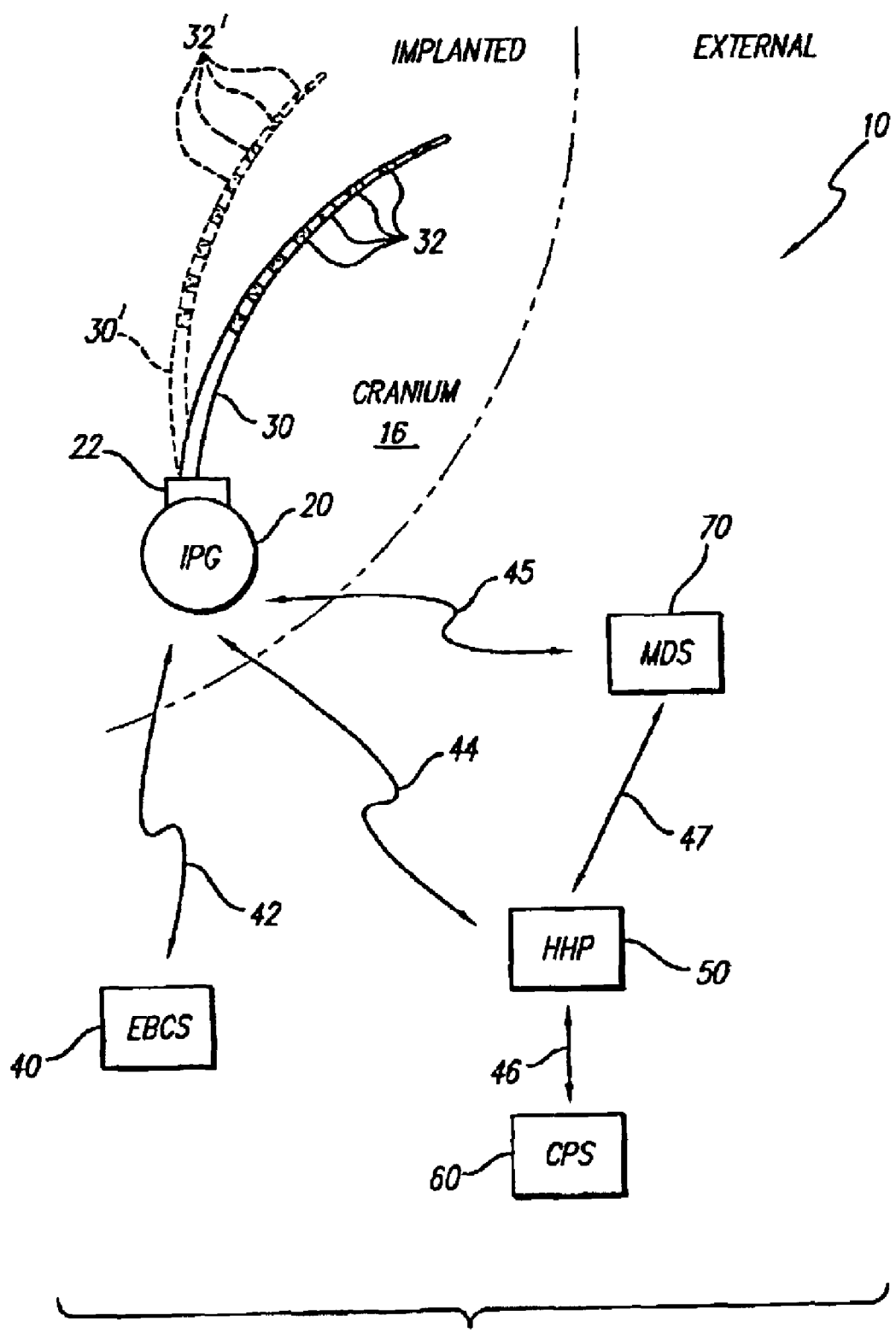
FIG. 1 illustrates the various components of a deep brain stimulation (DBS) system made in accordance with the invention.

A DBS system 10 made in accordance with the invention is illustrated in FIG. 1. The DBS system 10 includes an implantable pulse generator (IPG) 20 adapted to be implanted directly in or on the cranium 16 of a patient. At least one lead 30, having a plurality of electrodes 32 thereon, is attached to the IPG 20 via a suitable connector 22. Up to two separate leads 30 may be attached to the IPG 20. Hence, FIG. 1 shows (in phantom lines) a second lead 30', having electrodes 32' thereon, also attached to the IPG 20. Each lead includes at least two electrodes 32, and may include as many as sixteen electrodes 32. A preferred IPG 20 has four channels and can drive up to sixteen electrodes.

The IPG 20 includes a rechargeable battery. The battery is recharged, as required, from an external battery charging system (EBCS) 40, typically through an inductive link 42.

The IPG 20, as explained more fully below, includes a processor and other electronic circuitry that allows it to generate stimulus pulses that are applied to the patient through the electrodes 32 in accordance with a stored program. The IPG 20 is programmed and tested through a hand held programmer (HHP) 50; a clinician programming system (CPS) 60 that uses an HHP, or equivalent, to relay information; or a manufacturing and diagnostic system (MDS) 70.

The HHP 50 may be coupled to the IPG 20 via an RF link 44. Similarly, the MDS 70 may be coupled to the IPG 20 via another RF link 45. The CPS 60, which is coupled to the IPG 20 by way of the HHP 50, may also be coupled to the HHP 50 via an infra-red link 46. Likewise, the MDS 70 may be coupled to the HHP via another infra-red link 47. Other types of telecommunicative links, other than RF or infra-red may also be used for this purpose. Through these links, the CPS 60, for example, may be coupled through the HHP 50 to the IPG 20 for programming or diagnostic purposes. The MDS may also be coupled to the IPG 20, either directly through the RF link 45, or indirectly through the IR link 47 with the HHP 50.

Figure 2:
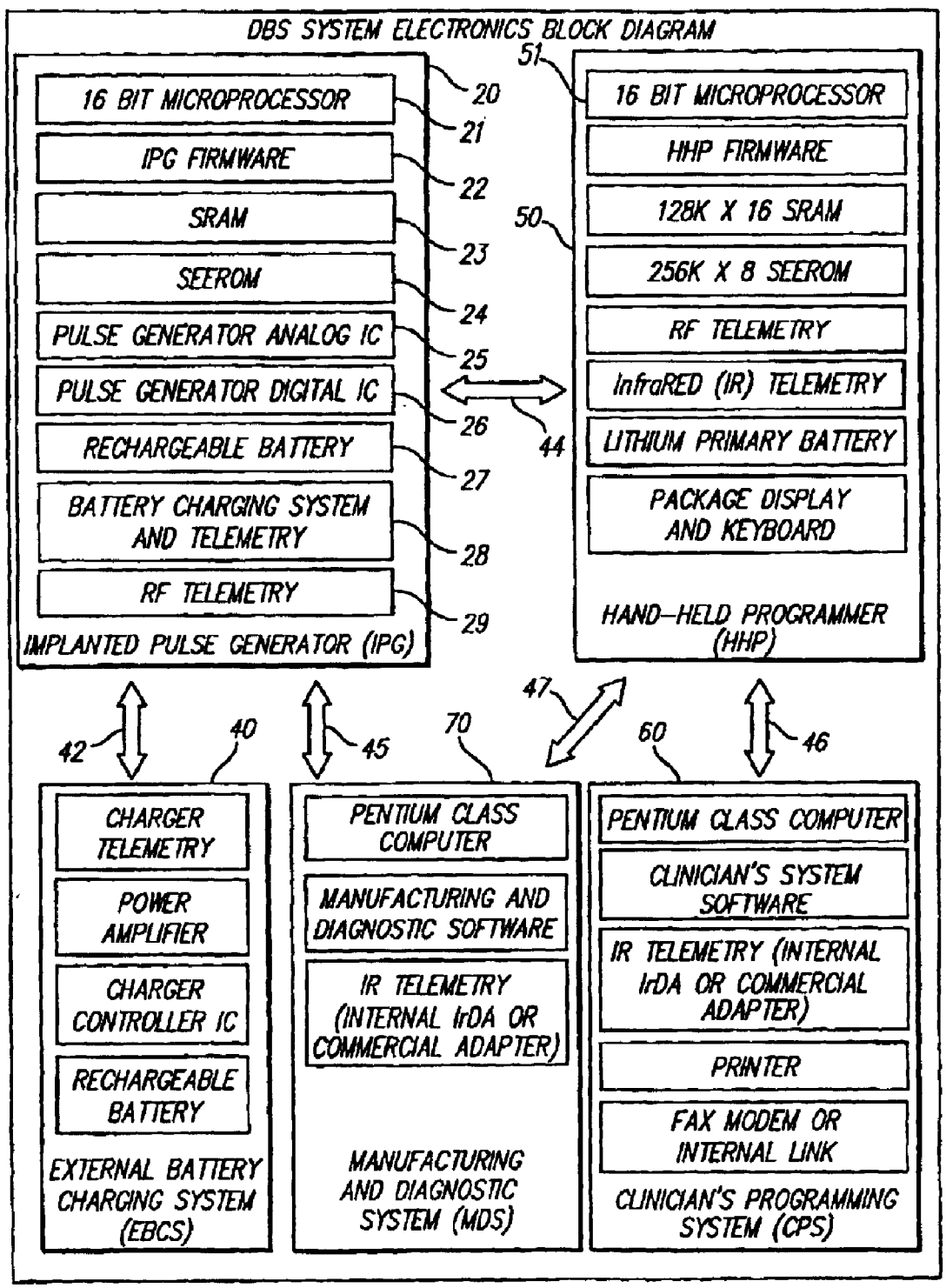
FIG. 2 is a block diagram of a DBS system of FIG. 1, and illustrates the various elements within each of the main sub-systems of the DBS system, which subsystems include an Implantable Pulse Generator (IPG), a Hand-Held Programmer (HHP), a Clinician's Programming System (CPS), a Manufacturing and Diagnostic System (MDS), and an External Battery Charging System (ECBS)

Turning next to FIG. 2, a block diagram of the DBS system 10 is illustrated, including the various elements within each of the main sub-systems of the DBS system. The subsystems of the DBS system 10 include an Implantable Pulse Generator (IPG) 20, a Hand-Held Programmer (HHP) 50, a Clinician's Programming System (CPS) 60, a Manufacturing and Diagnostic System (MDS) 70, and an External Battery Charging System (ECBS) 40.

As seen in FIG. 2, the IPG 20 includes various elements, including a microprocessor 21, IPG firmware 22, a SRAM memory 23 (which SRAM memory is optional, and may not be needed in some embodiments), a SEEROM memory 24, an analog IPG pulse generator integrated circuit (IC) 25 (which analog pulse generator circuit 25 functions as the output circuit of the IPG), a digital IPG pulse generator IC 26, a rechargeable battery 27, a battery charging system and telemetry circuit 28, and an RF telemetry circuit 29.

The microprocessor 21, in the preferred embodiment, comprises a 16 bit microprocessor and associated external controller based upon the VAutomation 8086 processor, or equivalent. Advantageously, this processor 21 is a flexible 16 bit processor that has been around for years and was the processor used in the IBM PC, thus many development tools are available for both software and hardware design for this device. The general performance-based features for the core and the additional peripheral devices in the mircoprocessor IC 21 are summarized as follows:

1. Core, Equivalent to Intel 8086 from Vautomation, or equivalent.
2. Operating Voltage: 2.2–3.5V
3. Oscillator—1.048 MHz crystal controlled oscillator, under 1 uA current consumption, 2.2–3.5V supply 4. Address Bus: 20 bit, non-multiplexed
5. Data Bus: 16 bit, non-multiplexed, supports multiplexed with CPU_ALE signal
6. Power Consumption: 300 uA @ 1 MHz main crystal frequency
7. Memory: ROM—1 Kbyte Mask ROM, containing bootstrap and initialization routines; SRAM—16 Kbyte, used for program and data space
8. External Memory: Provision for powering and reading from and writing to Atmel SEEPROM for operating system and initial parameter storage; Provision for None, 256 or 512 Kbytes external SRAM
9. Analog to Digital Converter: 12 bit, 4 channel signal multiplexer, 3 differential, 1 single-ended input signals, Vcc measurement—warm-up in 1 mS, Conversion time: <50 clocks (successive approximation), Programmable range and offset, External VRH and VRL, Separate VDD connection
10. Synchronous Serial Interfaces (2)—Clock and data in, clock and data out, handshake in and out
11. Piezo Buzzer control—7 bit tone register, bipolar or monopolar drive, 35568 Hz base block, tone is clock divided by 7 bit value in register, $8^{th}$ bit is on/off control
12. Interrupt Control—3 external interrupt request lines, high true
13. Invalid address detection non-maskable interrupt
14. External I/O Device select, low true
15. RF Telemetry: QFAST Modulation method with demodulator and RF mixer circuitry, Power control for external RF Circuitry, Antenna tuning control: 4 bits, Device ID registers: 24 bit, Timing Control for automatic receive, with clock pulse stealer circuitry for Time base adjustment, Data rate 512 bits per second to 8192 bits per second
16. Wakeup Timers: Timer 1–10 bit up-counter, 1 Hz drive, HIRQ on compare to value, then reset and up count again, range of programmable values is 3 sec to 1026 seconds; Timer 2–12 bit up-counter, 8 Hz drive, HIRQ on compare to value, then reset and up count again; Timer 3–12 bit up-counter, 1024 Hz drive, HIRQ on compare to value, then reset and count again
17. One-Minute Counter—modulo 60 counter driven by 1 Hz and HIRQ generator
18. Time of Day Registers
19. Watchdog monitor—Wakeup timer 1 interrupt signal is monitored and if two successive HIRQ3 signals are detected without proper watchdog supervision by the main processor then a system reset is asserted.
20. LCD Clock—clock line for external LCD display (to be used in HHP)
21. Test pins for system control bus visibility and debug
22. General purpose I/O used for pump control, but useful for other functions
23. Power On Clear Reset Circuitry The RF telemetry circuit 29 utilized within the IPG 20, in one preferred embodiment, is based on QFAST technology. QFAST stands for "Quadrature Fast Acquisition Spread Spectrum Technique", and represents a known and viable approach for modulating and demodulating data. The QFAST RF telemetry method is further disclosed in U.S. Pat. No. 5,559,828, incorporated herein by reference. The QFAST methodology utilizes an I/Q modulation and demodulation scheme that synchronously encodes clock and data onto a carrier signal of a suitable frequency, e.g., 262 KHz. The RF receive mixer and demodulator sections are implemented almost entirely on the Processor IC with only external receive amplifier circuitry and an antenna required to supplement the circuit. A method of tuning the antenna due to center frequency shifts upon laser welding the enclosure around the processor hybrid is implemented under software control. Pre-weld tuning is accomplished by the use of binary capacitors (capacitor chip arrays which are wire bonded during fabrication and tuned by testing and creating wire bonds as needed).

The RF carrier is derived from the processor system clock. In one embodiment, the system clock operates at 1.000 MHz. Other frequency ranges may be used, as needed. The data rate is adjustable by register control over a suitable range, e.g., from 512 to 4096 bits per second, and the range of the link at 4 kb/s (kilobits/second) through an 8 mil Titanium enclosure is greater than 40 inches.

Other components or elements within the IPG 20 may be conventional or as known in the art.

Still with reference to FIG. 2, the hand held programmer 50 is used by the patient to control the operation of the DBS Implantable Pulse Generator (IPG). The HHP functions as a small pager-like device which is designed to control the IPG. The HHP, in one embodiment, uses a 16 bit microprocessor 51 as its main controller. This microprocessor 51 may be the same as the microprocessor 21, used within the IPG 20, and thus has all of the benefits and features described previously. The following is a summary of the features of the HHP 50:
1. Package—central electronics volume is sealed against moisture ingress. Battery compartment is moisture resistant. ESD protection—Internal surfaces treated for ESD protection. Size—3.5"L×2.6"W×0.65"T; Shape—Landscape Pager.
2. LCD: Pixel area—128 columns by 55 rows; ICON area—above pixel area—time of day, month, date, activity Icon, battery warning, alarm warning, reservoir volume (battery charge); Interface—SPI, IIC or 8 bit parallel—SPI implemented to SSI of ASIC; Programming—bit mapped graphics instruction set; Contrast—hardware and software command; Power Consumption<20 uA ICON, <500 uA pixel area on.
3. Keyboard: Number of keys 5, one hidden; Action, any key can cause interrupt request, maskable; Seal/environmental—sealed to prevent moisture ingress, ESD shielded and debounced; Reset—Hardware reset if all five keys pressed together
4. Vibrator—A pager type vibrator motor is available for non-audible alerts to the user—Power Consumption—<60 mA, Control—single bit control
5. Audio transducer—Performance—>75 db spl output at 2 KHz; Power Consumption <10 mA, Control—7 bit register for tone control, 1 bit for on/off
6. IrDA Port—115 Kbit/s fixed data rate, IrDA 1.2 low power standard compliant. Can be powered down, as can UART. IrDA port receive line can be powered independently to see if external device needs attention even when UART is off.
7. Batteries and upconversion—Main Battery: lithium primary; Expected Battery Life—preferably more than 60 weeks, but at least 2 months at average current of 1 mA.
8. Processor 8086 core ASIC—see specification for Processor IC and VAutomation specification Memory: 1 Kbyte boot ROM, 16 Kbyte internal SRAM, 1 Mbyte External SRAM memory space, bank decoded into two pages, two 4 Mbit devices, accessible byte or wordwise; 512 K
9. External SEEPROM—four 64 Kbyte devices at address 0, 1, 2, 3.

The HHP 50 is designed to support multiple languages through the use of its graphics LCD and to display continuously basic status information about the implanted device and its own operation. The HHP 50 can perform RF telemetry to the IPG at the specifications mentioned above, as well as communicate over an IrDA 1.2 compatible infrared cable-less data link at 115 Kbaud over a 30 cm range. This range can be extended with the use of a commercially available IrDA 1.2 compliant serial port 8 foot expander which plugs into the 9 pin Sub-D connector found on personal computers and terminates with an IrDA transceiver.

As can be seen in FIG. 2, the DBS system 10 includes four major functional blocks: the Implanted Pulse Generator (IPG) 20; The Hand-Held Programmer (HHP) 50; The External Battery Charging System (EBCS) 40; and the Clinician's Programming System (CPS) 60. As previously indicated, the IPG 20 contains a 16 bit microprocessor 21, memory 23 and 24, a rechargeable battery 27 and custom pulse generation circuitry 25 and 26. Communication to the IPG 20 is via RF link 44 or other links 42 or 45. The HHP 50 takes the form of a small pager-like device, with an LCD graphics display and a simple and direct user interface and keyboard. The HHP 50 is able to communicate with the IPG 20 over a comfortable distance, e.g., up to 2 feet away, allowing the patient and clinician alike simple and efficient control of the IPG.

The CPS 60 is used by the clinician to fit the IPG 20 and electrodes 32 to the patient, and to record and document all stimulation settings. The CPS 60 communicates to the HHP 50 using an InfraRed wireless link 46, a standard in the computer industry. The HHP 50 communicates to the IPG 20 over an RF link 44. Secure communications without error are provided by utilizing a 24 bit identification code for all components in the system along with error detection codes embedded in all data packets submitted by any device in the system.

The HHP 50, in one embodiment, utilizes a label and membrane keypad to adapt to DBS applications. Software applicable to DBS is also used. The HHP 50 represents a general-purpose 8086-based product platform. Such platform is extremely flexible, yet meets the needs of small weight and size, rugged environmental protections and ease of use for the DBS application.

The packaging of the implanted pulse generator (IPG) 20 and its lead(s) 30 and electrodes 32 and electrode leadwire fixation system represent an important part of the system. A distally-located pulse generator has the luxury of available volume in which to house its power, electronics and control systems. A cranium mounted system, however, is greatly restricted in volume and depth. Yet, the IPG 20 has all of the features deemed important to the application within the volume constraints described.

The key features of the DBS system 10 shown in FIGS. 1 and 2 are summarized below:
1. DBS Implantable Pulse Generator (IPG) Features:
   a. 4 to 16 electrode contacts.
   b. 4 channels, comprised of any combination within the 16 contacts.
   c. Individual cathode and anode amplitude control.
   d. Rechargeable battery.
   e. Tool-less connector.
   f. Small package.
2. DBS Pulse Generator Performance—Rechargeable Battery
   a. Inductively charged from 2–3 cm.
   b. 80% charged in 4 hours.
   c. At 10 yrs, 1 channel typical discharge in approximately 30 days; 4 channels typical discharge approximately 7 days.
   d. IPG battery status monitoring with telemetry to hand held programmer (HHP).
   e. Battery control and safety circuitry for 100% failsafe operation.
3. DBS Pulse Generator Performance—Stimulation Capability
   a. Up to 16 electrodes and case ground, individually controlled: biphasic pulse current, frequency, pulse width, channel assignment, monopolar or multipolar operation.
   b. Up to 4 Channels: channel=common frequency and pulse duration for channel assigned electrodes (electrodes can operate in up to four channels).
   c. Amplitude: each electrode: 0–12 mA cathodic or anodic current in discrete steps, e.g., steps of 0.1 mA. Simultaneous output: ±20 mA (distributed)
   d. Pulse Width: 25 $\mu$s (microseconds) to 1 ms (millisecond), in 10 $\mu$s steps (equal for electrodes on a channel).
   e. Rate: 2 ranges including normal, 0–150 pps per channel in approximately 1 pps steps, and high rate (1 channel) 160–1200 in approximately 10 pps steps.
   f. Channel Timing: channel rates are regulated to prevent overlap with a method that is transparent to the patient.
   g. Anode Control: 3 modes—monopolar case (any electrode(s) (−) to case), passive anodes (electrodes connected to ground), and active anode with individual amplitude control.
   h. Charge Balance: assured through capacitor interface between electrode and output circuitry.
   i. Soft Start: from 1 to 10 seconds, in 1 second steps.
   j. Run Schedule: all channels of the implant turn on and off to the last stimulation settings at preset programmed times.
   k. Impedance: monopolar at 4 mA: 500 Ohms typical.
4. DBS Pulse Generator Performance—Telemetry Output
   a. Battery Capacity: automatic telemetry data retrieval initiated by external programmer communication.
   b. Electrode Impedance: automatic telemetry data retrieval initiated by external programmer communication.
   c. Confirmations: programmable parameter changes from external equipment confirmed with back telemetry.
   d. Programmed Settings: automatic telemetry data retrieval of all programmable settings initiated by external programmer communication.
5. DBS Pulse Generator Performance—Connector
   a. Two feedthroughs with up to 16 total electrical contacts for a removable lead system with strong, reliable electrical performance (low current spread) under implanted conditions.
   b. Although the connection is typically made only once for any device, the connector mechanism is designed to withstand a minimum of 10 connections.
   c. The lead connector system utilizes a simple method to secure the electrode leadwire without the use of a tool.
6. DBS Patient Programmer Features
   a. Intuitive user interface.
   b. Back-lighted flat panel screen.
   c. Hidden physician screen.
   d. 2–3 foot RF range.
   e. Implant battery monitor.
   f. Run time scheduler.

g. 4 program storage.

h. Infrared communication link to clinician's programming system.

Figure 3:
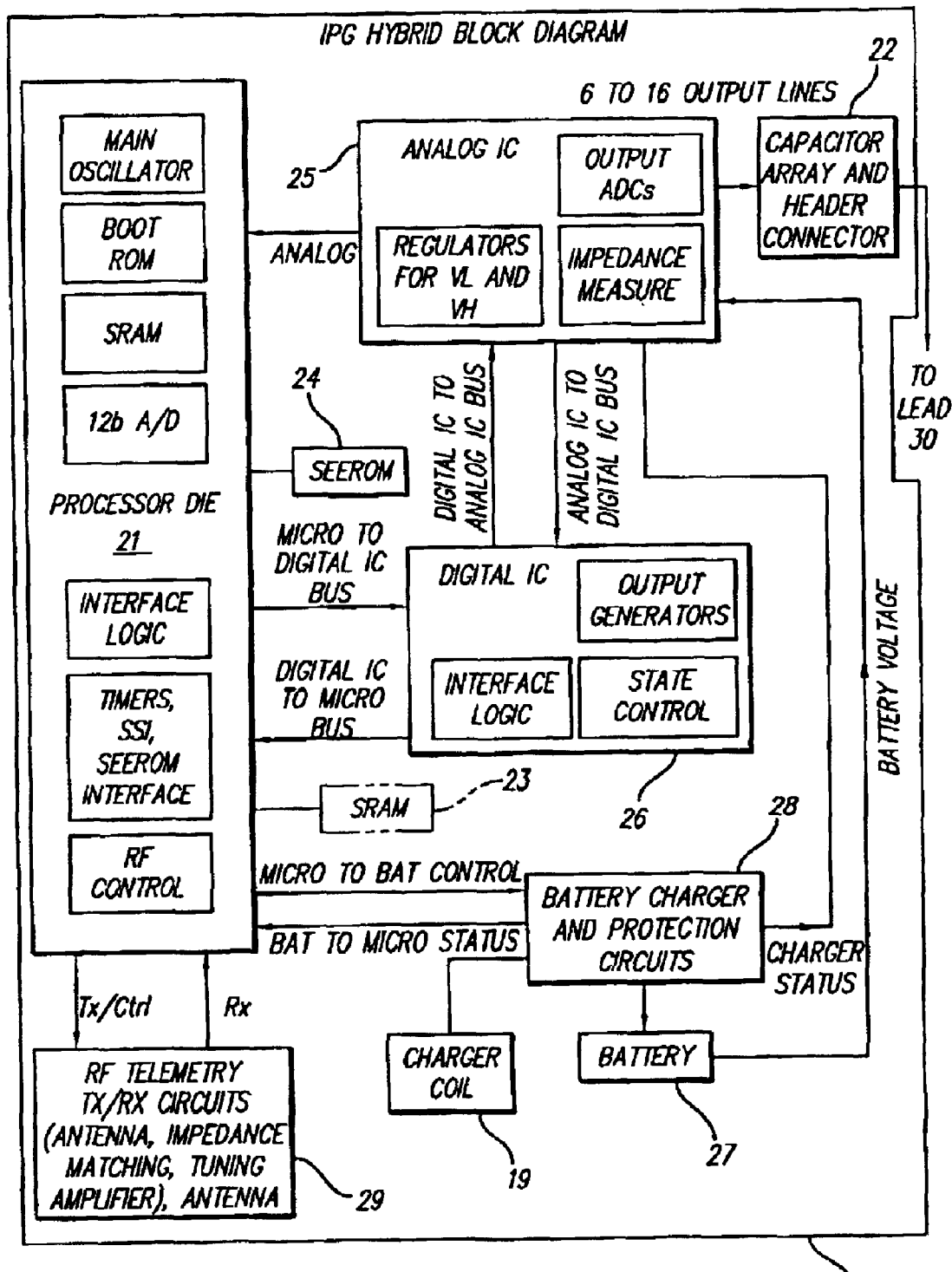
FIG. 3 is a block diagram of the IPG of FIG. 2.

A block diagram showing the hybrid configuration of the IPG 20 in accordance with a preferred embodiment of the invention is shown in FIG. 3. As seen in FIG. 3, the microprocessor 21 lies at the heart of the IPG. RF telemetry TX/RX Circuits 29 interface with the processor 21. Included in the telemetry circuits 29 are an antenna, impedance matching tuning amplifier, and the like.

SRAM memory 23, when used, and SEEROM memory 24 provide storage for data and control signals associated with the operation of the processor 21.

The processor 21 controls digital IC 26 and directs it to generate appropriate stimulation currents for delivery through the leads 30 and 30' and electrodes 32 and 32'. The digital IC 26, in turn, controls analog IC 25 so as to generate the stimulus currents. Connection with the lead(s) 30, 30' is made through a capacitor array, so that all electrodes are capacitor coupled. A header connector 22 facilitates detachable connection of the lead(s) 30, 30' with the IPG 20.

A rechargeable battery 27, e.g., a lithium-ion battery, powers operation of the IPG 20. A charger coil 19 provides a means for coupling energy into the battery for recharging. Battery charger and protection circuits 28 receive the power for recharging the battery through the charger coil 19; regulate and distribute power to the rest of the IPG 20, as required, and monitor the status of the rechargeable battery 27.

While the invention herein disclosed has been described by means of specific embodiments and applications thereof, numerous modifications and variations could be made thereto by those skilled in the art without departing from the scope of the invention set forth in the claims.

What is claimed is:

1. A multichannel deep brain stimulation system (10) comprising:

an implantable pulse generator (20) having means for generating electrical stimuli comprising a plurality of channels and memory circuits, wherein the memory circuits store at least one program and data;

at least one electrode array (30) connected to said implantable pulse generator, said at least one electrode array having a plurality of electrodes (32);

a rechargeable battery (27) coupled to the implantable pulse generator, a hand-held programmer (50);

a clinician's programmer (60);

a manufacturing and diagnostic system (70); and an external battery charging system (40);

wherein the implantable pulse generator (20) and said at least one electrode array (30) are adapted to be implanted directly in the cranium of a patient; and wherein the means for generating electrical stimuli comprises control circuits (21, 28, 27) and the memory circuits (22, 24) that cause stimulation pulses having parameters specfied by the at least one program and data stored in the memory circuits to be applied through at least one of the plurality of channels to the electrodes (32) of the at least one electrode array; and wherein the hand-held programmer (50) is adapted to: communicate with the implantable pulse generator, allow the patient to monitor and change stimulation parameters, provide a first communication link (46) with the clinician's programmer, and provide a second communication link (47) with the manufacturing and diagnostic system, all for the purpose of programming and testing the implantable pulse generator (20); and wherein the external battery charging system (40) is adapted to be inductively coupled to the rechargeable battery (27) for the purpose of replenishing the power stored within the rechargeable battery.

2. The deep brain stimulation system of claim 1 wherein the manufacturing and diagnostic system further includes means for coupling with the implantable pulse generator (20) via RF communication.

3. The deep brain stimulation system of claim 2 wherein the second communication link between the manufacturing and diagnostic system and the hand held programmer comprises an infra-red communication link.

4. The deep brain stimulation system of claim 1 wherein said at least one electrode array comprises at least two electrode arrays (30,30'), thereby facilitating bilateral stimulation of the brain of the patient.

5. The deep brain stimulation system of claim 4 wherein each of the electrode arrays (30 and 30') includes at least two and as many as sixteen electrodes (32, 32').

6. The deep brain stimulation system of claim 1 wherein the first communication link between the clinician programmer and the hand-held programmer comprises an infra-red communication link.

7. The deep brain stimulation system of claim 1 wherein the implantable pulse generator comprise a header connector (22), and wherein the at least one electrode array is detachably connected to the implantable pulse generator through the header connector.

8. The deep brain stimulation system of claim 7 wherein the implantable pulse generator includes an output circuit (25), and wherein the at least one electrode array (30) is capacitively coupled to the output circuit (25) of the implantable pulse generator.

9. A multichannel bilateral deep brain stimulation system (10) comprising:

an implantable pulse generator (20);

a plurality of electrode arrays (30, 30'), each of said plurality of electrode arrays having a plurality of electrodes (32) thereon, and each of said plurality of electrode arrays being detachably connected to said implantable pulse generator;

processing means (21, 26, 27) and memory means (22, 24) included within the implantable pulse generator, the memory means comprising memory circuitry wherein at least one stimulation program and data are stored, wherein the implantable pulse generator is adapted to generate and apply stimulation pulses to selected electrodes (32) of the plurality of electrode arrays as defined by the at least one stimulation program and data stored within the memory means;

a hand held programmer (50);

a clinician programmer (60);

a manufacturing and diagnostic system (70);

a rechargeable battery (27) included within the implantable pulse generator that provides operating power for the implantable pulse generator;

means (50) for non-invasively programming the memory circuitry with the at least one stimulation program and data;

means for providing a first radio frequency (RF) communication link between the implantable pulse generator and the hand held programmer;

means for providing a first infra red communication link between the hand held programmer and the clinician programmer;

means for providing a second infra red communication link between the hand held programmer and the manufacturing and diagnostic system;

means for providing a second RF communication link between the implantable pulse generator and the manufacturing and diagnostic system; and means (40) for non-invasively recharging the rechargeable battery;

wherein the hand held programmer includes means for allowing the patient to monitor and change the at least one stimulation program and data, and further facilitates communications between the clinician's programmer, the manufacturing and diagnostic system and the implantable pulse generator.

10. The deep brain stimulation system of claim 9 wherein each of the electrode arrays (30, 30') includes at least two and as many as sixteen electrodes (32, 32').

11. The deep brain stimulation system of claim 9 wherein the implantable pulse generator comprises a header connector (22), and wherein each of said plurality of electrode arrays is detachably connected to the implantable pulse generator (20) through the header connector (22).

12. The deep brain stimulation system of claim 11 wherein the implantable pulse generator includes an output circuit (25), and wherein the at least one electrode array (30) is capacitively coupled to the output circuit (25) of the implantable pulse generator.

13. A multichannel deep brain stimulation system comprising:

a cranium mountable implantable pulse generator including at least one memory circuit;

data stored within the at least one memory circuit;

at least one electrode array adapted to be detachably connected to the implantable pulse generator, the at least one electrode array including two or more electrodes thereon;

a rechargeable battery coupled to the implantable pulse generator;

an external battery charging system;

a hand held programmer;

a clinician's programmer;

a manufacturing and diagnostic system;

wherein the implantable pulse generator includes means for generating electrical pulses that are defined by parameters specified by the data stored in the at least one memory circuit; wherein the hand held programmer includes means for communicating with the implantable pulse generator, and further includes means for allowing a patient to monitor and program at least some of the data stored in the at least one memory circuit;

wherein the hand held programmer further includes means for communicating with the clinician's programmer, whereby an operator of the clinician's programmer communicates with and programs the implantable pulse generator through an interface provided by the hand held programmer; and wherein the hand held programmer also includes means for communicating with the manufacturing and diagnostic system, whereby a user of the manufacturing and diagnostic system monitors and communicates with the implantable pulse generator through an interface provided by the hand held programmer.

14. The system of claim 13 wherein the implantable pulse generator includes at least two channels, wherein the two or more electrodes of the at least one electrode array are adapted to be assigned to any of the at least two channels, and wherein each of the at least two channels is adapted to define a common frequency and pulse duration for the two or more electrodes when such electrodes are assigned to an associated channel.

* * * * *